US00PP13680P29

(12) United States Plant Patent
Berry

(10) Patent No.: US PP13,680 P2
(45) Date of Patent: Mar. 25, 2003

(54) *TERNSTROEMIA GYMNANTHERA PLANT NAMED 'SOTALL'*

(75) Inventor: James Bryan Berry, Daphne, AL (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 10/147,464

(22) Filed: May 17, 2002

(51) Int. Cl.[7] ..... A01H 5/00
(52) U.S. Cl. ..... Plt./226
(58) Field of Search ..... Plt./226

*Primary Examiner*—Kent Bell

(57) ABSTRACT

A new and distinct variety of *Ternstroemia gymnanthera* plant named 'Sotall', characterized by its uniformly dense, upright and oval growth habit, foliage size, and foliage color.

2 Drawing Sheets

BACKGROUND OF THE INVENTION

The present invention relates to a new and distinct cultivar of Ternstroemia, botanically known as *Ternstroemia gymnanthera*, and herein referred to by the cultivar name 'Sotall'. This new Ternstroemia variety was discovered by James Bryan Berry in October, 1995 as an openly pollinated seedling in a group of unnamed, unpatented *Ternstroemia gymnanthera* plants at Plant Development Services Inc. in Loxley, Ala. The value of this new cultivar lies in its uniformly dense, upright and oval growth habit, foliage size, and foliage color. The new variety has retained many of the outstanding attributes of its parent species, in particular its tolerance of insects and disease, which makes it adaptable to culture in the Sunbelt states.

Asexual propagation of the new plant by cuttings has been under Mr. Berry's direction at the same location. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in Loxley, Ala.

1. A uniformly dense, upright and oval growth habit 12–14' tall and 5–6' wide.
2. Attractive, large glossy green foliage.
3. Fast growth rate under normal fertilization and moisture conditions.
4. Easily trained into a small tree.
5. Good specimen plant.
6. Hardy to Zone 7.
7. Performs well in sun or shade.
8. Resistant to fungal leaf spot.
9. Resistant to insect pests, such as aphids and scale.
10. Very desirable in planters.
11. Makes a very good formal or informal hedge or screen.
12. Very good foundation plant for large buildings or corner plant for homes.
13. Has the ability to be sheared and trimmed to be kept within prescribed limits.

14. Easily propagated with semi-hardwood cuttings in late summer through the fall.
15. Withstands city conditions.

DESCRIPTION OF THE DRAWINGS

This new variety of *Ternstroemia gymnanthera* is illustrated by the accompanying photographic prints in which:

1. The photograph at the top of the first sheet is a close-up showing the foliage and stem color of the new variety in early fall.

2. The photograph at the bottom of the first sheet shows the uniform growth habit and foliage color of a group of young 7 gallon plants.

3. The photograph at the top of the second sheet is a side-by-side photograph, from left to right, of the patented variety *Ternstroemia gymnanthera* 'Contherann' U.S. Plant Pat. No. 11,737 and the new variety in mid-winter.

4. The photograph at the bottom of the second sheet shows the uniformly dense, upright and oval growth habit of a crop of ten gallon plants.

The colors shown are as true as is reasonably possible to obtain by conventional photographic procedures. Colors in the photographs may appear different than actual colors due to light reflectance. The colors of the various plant parts are defined with reference to The Royal Horticultural Society Color Chart. Description of colors in ordinary terms are presented where appropriate for clarity in meaning.

BOTANICAL DESCRIPTION OF THE PLANT

The following is a detailed description of the new variety of Ternstroemia based on my observations made of 3 year old plants grown in 7 gallon containers in wholesale commercial production practices, in greenhouses, and in established landscape plantings in Loxley, Ala.

Distinctive Characteristics

| Characteristic | *Ternstroemia gymnanthera* (The Species) | *Ternstroemia g.* 'Contherann' U.S. Plant Pat. No. 11,737 | *Ternstroemia g. Scotall'* |
|---|---|---|---|
| Height (Mature) | 8–10' | 10–12' | 12–14' |

-continued

| Characteristic | *Ternstroemia gymnanthera* (The Species) | *Ternstroemia g.* 'Contherann' U.S. Plant Pat. No. 11,737 | *Ternstroemia g. Scotall'* |
|---|---|---|---|
| | Distinctive Characteristics | | |
| Width (Mature) | 5–6' | 6–7' | 5–6' |
| Leaf Length | 2½–4" | 2¼–3" | 2½–3¼ |
| Leaf Width | ½–1½" | ¾–1⅛" | 1 3/16–1½" |
| Leaf Shape | oblong to lanceolate | narrowly oblanceolate | broadly oblanceolate |
| Leaf Color (immature) | Yellow-Green Group 146A | Greyed-Red Group 178A | Yellow-Green G. 146A |
| Leaf Color (mature) | Green Group 137A | Green Group 137A | Green Group 137A |
| Leaf Color (fall/Winter) | Greyed-Orange G. 166A | Greyed-Purple G. 187A | Greyed-Orange G. 175C |

Ternstroemia 'Sotall' can be compared to the patented plant Ternstroemia 'Contherann' U.S. Plant Pat. No. 11,737 and the species *Ternstroemia gymnanthera*, however, in side-by-side comparisons conducted in Loxley, Ala., there are many differences. As indicated above, 'Sotall' has a more upright growth habit, and a more uniform foliage size, shape, and color. Ternstroemia 'Sotall' also differs from *Ternstroemia gymnanthera* 'Contherann' U.S. Plant Pat. No. 11,737 in that the younger foliage does not have the intense red and purple fall and winter color. In the nursery industry *Ternstroemia gymnanthera* is traditionally grown from seed which results in a tremendous amount of variation.

The seed parent of 'Sotall' is an unpatented plant of Theaceae *Ternstroemia gymnanthera*. There is confusion in the nursery trade in that what is called *Cleyera japonica* is actually *Ternstroemia gymnanthera*. Although similar, they differ in many ways. *Cleyera japonica* has a larger leaf 3–6" long and ¾–2" wide with an accuminate tip compared to 2½–4" long and ½–1½" wide with an obtuse tip. *Cleyera japonica* also has 25 stamens in one series unlike *Ternstroemia gymnanthera* which has nore than 25 stamens in two or more series.

CLASSIFICATION

Botanical: *Ternstroemia gymnanthera* 'Sotall'.
Parentage: Chance seedling of *Ternstroemia gymnanthera*.
Commercial: Broadleaf evergreen.
Form: Upright, dense, and globose.
Height: 12–14'.
Width: 5–6'.

Growth rate: Fast under normal fertilization and moisture conditions. Semi-hardwood cuttings taken in late summer through the fall produce rooted cuttings in three to four months in Loxley, Ala. Root development is vigorous and finely branched. In a period of four years from a rooted cutting the plant reaches a height of 5 to 6 feet and a spread of 3 to 4 feet. The plant normally grows at the rate of about 18 inches or more per year and reaches a height of 14 feet and a spread of six feet at maturity. A dense habit is maintained due to the abundant branch development.

Foliage: Alternate, simple, evergreen, leathery, glabrous, broadly oblanceolate, 2½ to 3¼" and 1 3/16 to 1½" wide, apex obtuse, base cuneate and margins are entire. Immature petioles are Yellow-Green Group 144A maturing to ⅛ to 3/16" long and Greyed-Purple Group 185C. The upper surface of the immature leaf is Yellow-Green Group 146A. The underside is Yellow-Green Group 146B and matte. The immature upper surface midribs are Yellow-Green Group 144A and mature to Yellow-Green Group 146D. The veins, other than the midrib, are generally not visible on the upper surface or the underside of the leaf. The leaf matures to Green Group 137A upper surface and Yellow-Green Group 146C on the underside. With the onset of cool weather in the fall, some of the immature foliage darkens to Greyed-Orange Group 175C and the mature foliage remains at Green Group 137A. There are occasional alternate foliaceous stipules which are ¼ to ½" long and 1/16 to ⅛" wide. The upper surface is Yellow-Green Group 144A and the underside is Yellow-Green Group 144B. The stipules are non-caducous.

In 1998, the date of initial spring growth was March 5, in Loxley, Ala. After the initial spring flush there was almost continuous growth until fall ending October 27, also in Loxley, Ala. This growth pattern was identical to the parent species. When grown in full sun, the internode length of this plant is ¼" to ⅝" which is similar to the parent species. When grown in light shade the internode length is ⅝" to 1¼" which is also similar to the parent species. As would be expected, either plant grown in the shade results in a taller, less dense plant with larger leaves.

The average length of terminal growth of the initial spring flush is about 5 to 6" for a plant in full sun and about 6 to 7" when grown in shade. The length of each growth flush is 2 to 4" longer than the growth flush of the parent species resulting in a larger plant more quickly. There are usually 4 to 6 flushes of growth per year under ideal growing conditions in Loxley, Ala. With each flush there is a 2 to 3½" stem which produces only foliaceous stipules. The true leaves are clustered at the end of each flush of growth with a whorled appearance. Each flush produces 1 to 7 branches which is similar to the parent species. Very little trimming is needed to produce a dense 26" tall and 22" wide three gallon plant during the growing season. *Ternstroemia gymnanthera* seedlings grown under identical conditions were vey inconsistent in vigor and color.

Although there are many variables involved, it should take about 8 to 10 years for this plant to reach a mature height of 12 to 14' and width of 5 to 6'. In the landscape little or no pruning is necessary to produce a dense, upright, and globose shrub in full sun. In shade, however, some trimming may be needed to produce the same effect.

Stems: The young shoots are Yellow-Green Group 144A, glabrous, and matte. The mature stems are Greyed-Green Group 197A, glabrous and rugose. The pith is solid and uniform.

Flowers: Axillary, solitary, bisexual, small, slightly fragrant, yellowish white and ½ to ¾" across. The inconspicuous flowers are produced from May to June on the previous year's wood or on short current season spurs. Buds are globular, Yellow-Green Group 145A, and without foliaceous appendages. Unbranched pedicels are ½ to ¾" long, curved near the end, and also Yellow-Green Group 145A. There are 5 sepals which are united at the base and 5 petals arranged regularly, united at the base, and imbricate in bud. There are 25 to 40 stamens in 2 to 3 series, and the anthers are glabrous, apiculate, and basifixed. As the flower opens the petals are Yellow-Green Group 145C and the pollen is Yellow Group 2D. The blooms last on the plant in the garden 3 to 6 days. A mature plant may have several hundred flowers.

Fruit: Indehiscent, berrylike, globose to ovoid, ½" diameter, 1" long; seeds usually 2–3 and Orange-Red Group 34A when mature. Immature fruit are Yellow-Green Group 146D maturing to Red Group 46B in late summer or early fall.

Culture: Grows well in a wide range of conditions and tolerates sun to shade. Grows in nearly any soil type, from moist to dry and sand to clay. Very heavy clays should be amended with peat moss, compost, or shredded pine bark to improve the soil texture. Poorly drained locations should be avoided. Responds well to mulching and medium applications of fertilizer; prefers ph 5 to 6.5. Very little pruning is needed, however, the plant can be sheared and maintained as a 5 to 6' shrub or pruned up into a small tree. Adaptable to containers and above ground planters. Propagated with semi-hardwood cuttings in late summer through the fall.

Pests: None observed to date.

I claim:

1. A new and unique variety of *Ternstroemia gymnanthera* plant named 'Sotall' as herein shown and described.

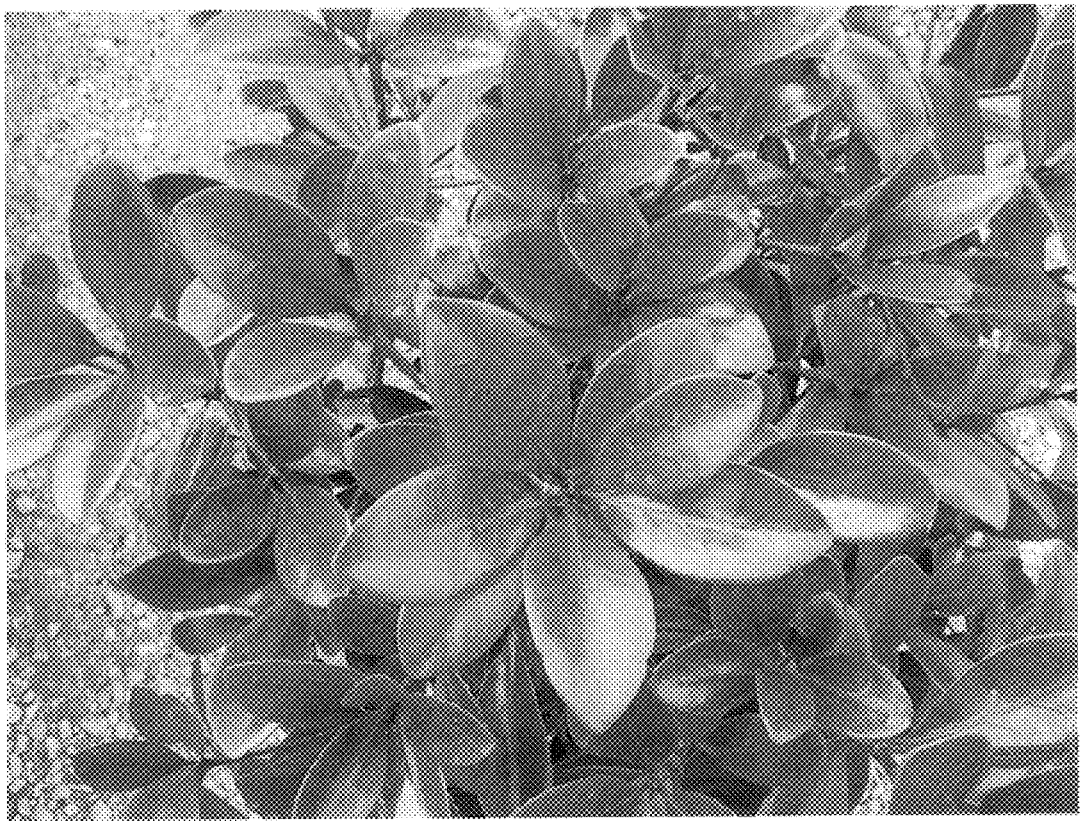
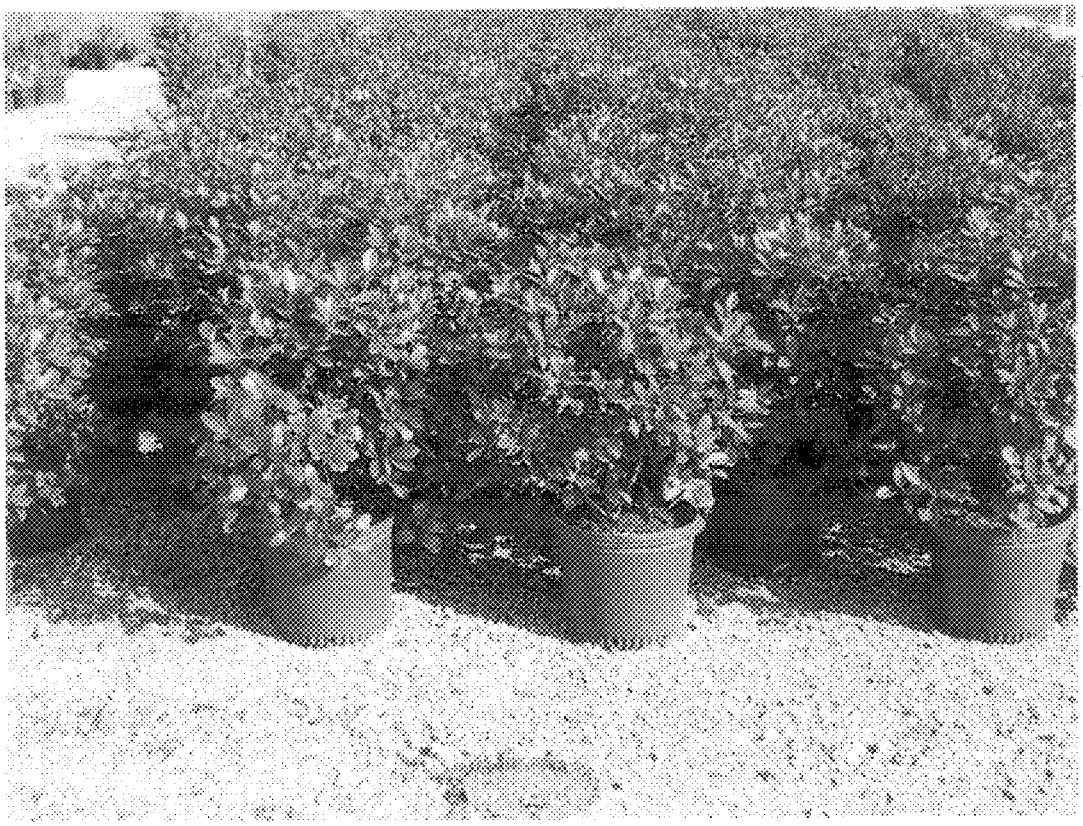

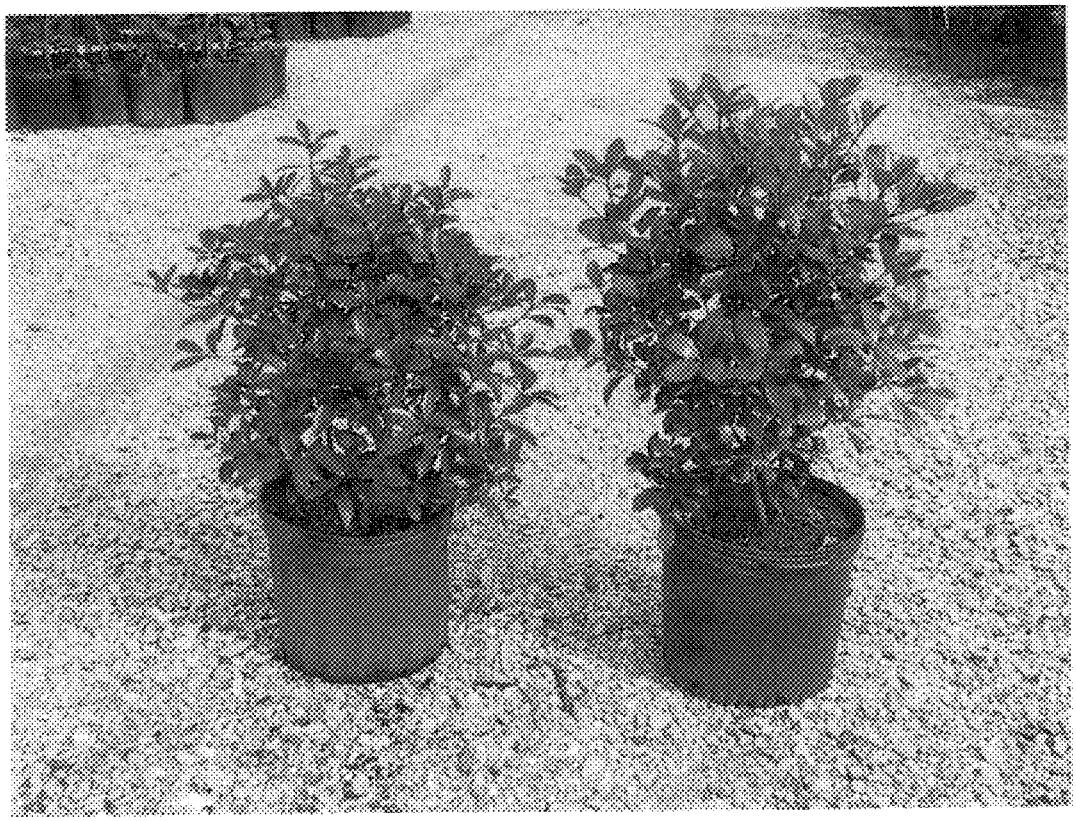
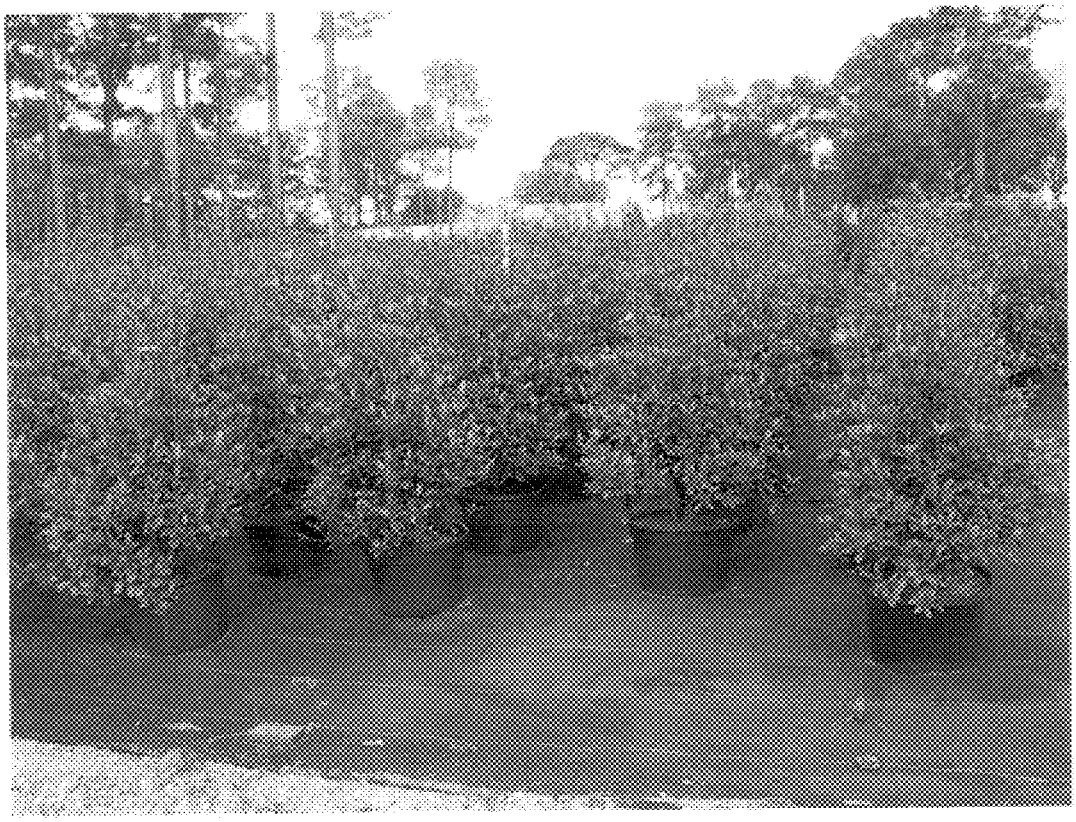

* * * * *